United States Patent [19]
Rohrer et al.

[11] Patent Number: 4,599,216
[45] Date of Patent: Jul. 8, 1986

[54] APPARATUS FOR EXPOSURE TO MICROWAVES

[75] Inventors: Michael D. Rohrer, Norman; Ronald A. Bulard, Oklahoma City, both of Okla.

[73] Assignee: Board of Regents for the University of Oklahoma, Norman, Okla.

[21] Appl. No.: 553,788

[22] Filed: Nov. 21, 1983

[51] Int. Cl.⁴ .............................. A16L 2/00; B01J 1/10
[52] U.S. Cl. .................................... 422/21; 422/186; 422/209
[58] Field of Search ................... 210/748; 422/21, 186, 422/209

[56] References Cited
U.S. PATENT DOCUMENTS 3,494,722  2/1970  Gray ....................................... 422/21
3,885,915  5/1975  Utsumi et al. ......................... 422/21
3,926,556 12/1975  Boucher ................................ 422/21

FOREIGN PATENT DOCUMENTS 1294829 11/1972 United Kingdom ................... 422/21

OTHER PUBLICATIONS

Kahler et al., The Nature of the Effect of a High-Frequency Electric Field Upon Paramoecium. Public Health Rep.; Vol. 44:339–347, 1929.
Beckwith et al., Ultrasonic Radiation and Yeast Cells. Proc. Soc. Exptl. Biol. Med., 29:362–364, 1931.
Fleming, Effect of High-Frequency Fields on Microorganisms. Elec. Eng., Vol. 63(1); 18–21, 1944.
Brown et al. An Exploration of the Effects of Strong Radiofrequency Fields on Microorganisms in Aqueous Solutions. Food Technology, Vol. 8:361–366, 1954.
Teixeira-Pinto et al. The Behavior of Unicellular Organisms in an Electromagnetic Field. Exper. Cell Research; 20:548–564, 1960.
White et al. Report on Effect of Cooking by Radiofrequency Waves on Bacteria in Food. Monthly Bulletin of the Ministry of Health and the P.H. Laboratory Sewe., Vol. 21–22:227–236, 1962.
Grecz et al. Effect of Radiofrequency Energy (2450mc) on Bacterial Spores. Bacteriol. Proc.; p. 145, 1964.
McLellan et al. Effects of Microwave Cookery on the Bacterial Counts of Food. Journal of Applied Bacteriology, vol. 28:331–335, 1965.
Lacey et al., Effects of Microwave Cookery on the Bacterial Counts of Food, J. Appl. Bact.; 28(2):331–335, 1965.
Olsen, Microwaves Inhibit Bread Mold, Food Engineering; Jul.:51–53, 1965.
Takashima, Studies on the Effect of Radiofrequency on Biological Macromolecules, IEEE Trans. Bio.-Med. Eng., 13:28–31, 1966.
Goldblith, Basic Principles of Microwaves and Recent Developments, Advan. Food Res., 15:277–301, 1966.

(List continued on next page.)

[57] ABSTRACT

The three dimensional movement of items to be exposed to microwave irradiation is facilitated by the apparatus of the present invention which provides for the turningly rotating exposure of such items to microwave irradiation. The microwave sterilization of items and fixation of eucaryotic cell specimens may be accomplished by such microwave irradiation. A kit of spore samples may be used to determine sterilization efficiency of particular microwave ovens.

The apparatus for facilitating the exposure of items to microwave irradiation comprises a base; a plate having a substantially horizontal plane and being rotatably mounted on said base; a spit comprising an axis and being turnably mounted on said plate in a manner substantially axially parallel to the horizontal plane; a means for mounting items upon the spit; a means for rotating the plate in the horizontal plane while turning the spit with items mounted thereon and a means for determining a sterilization efficiency in said microwave oven. A method for sterilizing items or fixating eucaryotic cells emplaced within the above described apparatus. An indicator strip to signify exposure to microwave irradiation.

21 Claims, 3 Drawing Figures

OTHER PUBLICATIONS

Goldblith et al., Effect of Microwaves on *Escherichia coli* and *Bacillus subtilis,* Appl. Microbiol., 15:1371–1375, 1967.

Delany et al., Microwave Energy Appl. Newsletter, vol. 1, p. 11, 1968.

Lechowich et al., Procedure for Evaluating the Effects of 2,450 Megahertz Microwaves Upon *Streptococcus faecalis* and *Saccharomyces cereisiae,* Appl. Microbiol., 17:106–110, 1969.

Culkin et al., Destruction of *Escherichia coli* and *Salmonella typhimurium* in Microwave-Cooked Soups, Journal of Milk and Food Technol., vol. 38;8–15, 1975.

Latimer et al., Microwave Oven Irradiation as a Method for Bacterial Decontamination in Clinical Microbiology Laboratory, Journal of Clinical Microbiology, 6:340–342, 1977.

Wood, Microwave Sterilization of Tissue Culture Media. Hort. Science; vol. 16(3):417–418, 1981.

Sanborn et al., Microwave Sterilization of Plastic Tissue Culture Vessels for Reuse, Appl. and Environmental Microbiology, 44:960–964, 1982.

Zimmerman et al., Fast Fixation of Surgical Pathology Specimens, Lab. Med., 3:29–30, 1972.

Emerson, Electromagnetic Wave Absorbers and Anechoic Chambers Through the Years, IEEE Transactions, vol. AP-21, No. 4, Jul., 1973.

Bernard, Microwave Irradiation as a Generator of heat for Histological Fixation, Stain Technology, vol. 49:215–224, 1974.

Petrere et al., Microwave Fixation of Fetal Specimens, Stain Technology, vol. 52:113–114, 1977.

Login, Microwave Fixation Versus Formalin Fixation of Surgical and Autopsy Tissue, American Journal of Medical Technology, vol. rr:435–437, 1978.

Patterson et al., Microwave Fixation of Cells in Tissue Culture, Stain Technology, 55:71–75, 1980.

Patterson et al., Fixation of Cells in Tissue Culture by Microwave Irradiation, Journal of Tissue Culture Methods, vol. 6(1):1–3, 1981.

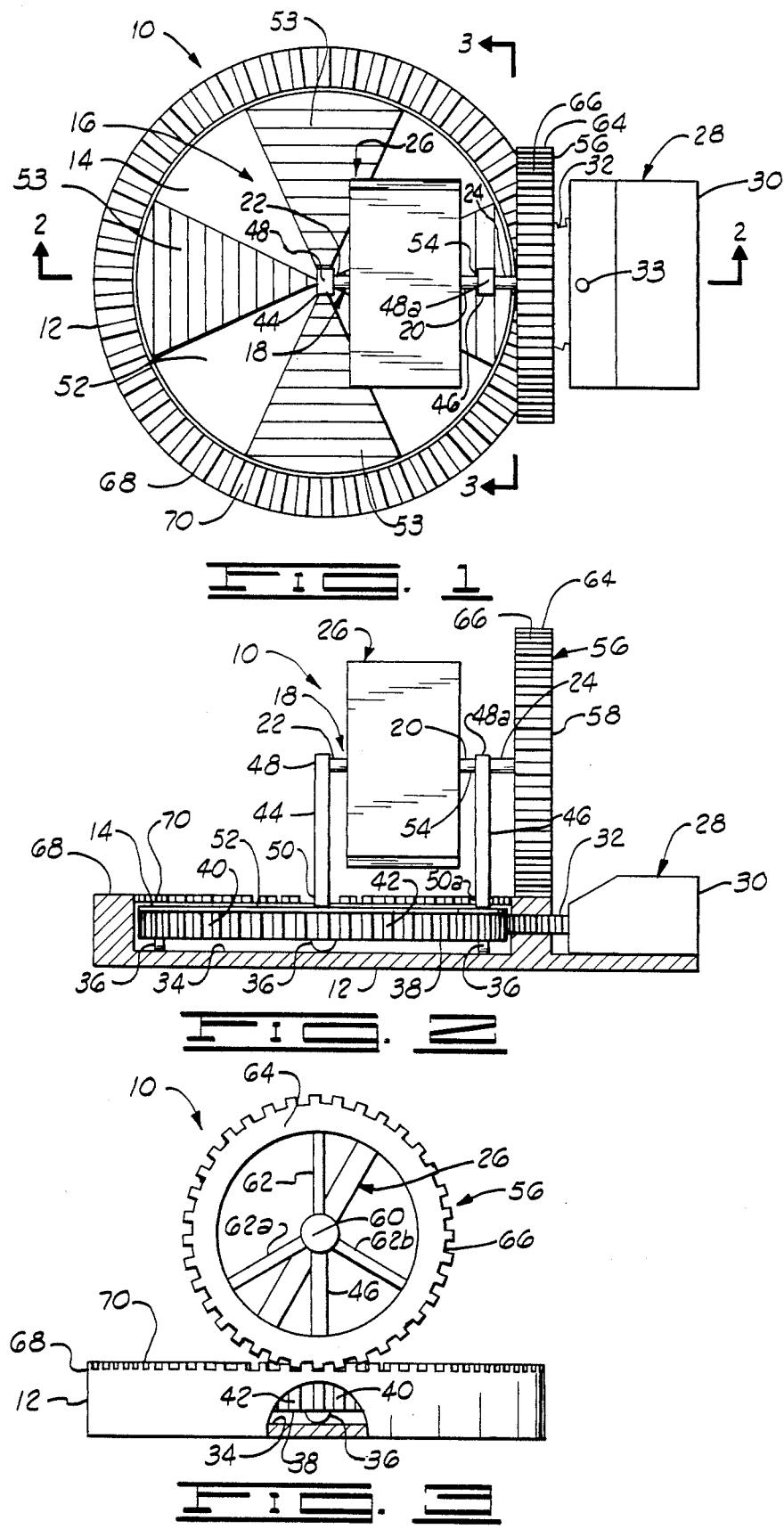

APPARATUS FOR EXPOSURE TO MICROWAVES

BACKGROUND OF THE INVENTION

There exists a need for sterile items in many areas of endeavor. The dental and medical fields in particular represent areas in which sterile items are often desired for use in patient care. Even homelife sometimes presents situations where sterile items would be desirable. There is, therefore, a manifold need for methods of sterilization usable in the above described fields or situations.

The generally acknowleged most reliable method of sterilization is autoclaving, which entails the heating of items to at least about 120° C. in a steam saturated atmosphere for periods of time ranging from about ten minutes to one day or more. Autoclaving, of course, to maintain the above conditions, requires the use of an autoclave which is not always available to those in need thereof. The damp heat of an autoclave is also known to have deleterious effects such as metal corrosion, thermal warping of plastics and inoperativeness of closely fitting parts in tools such as turbine-driven dental handpieces.

Another method of sterilization commonly utilized is dry heat. While dry heat does not usually cause metal corrosion, studies have indicated that sterilization in heating ovens requires lengthy periods of heating. Thermally induced warping of materials and charring of paper and cotton materials also may result from dry heating.

The use of gaseous ethylene oxide to sterilize objects, while not usually harming materials such as metals or items such as dental handpieces, does involve a two to eight hour sterilization time, in addition to a subsequent period of aeration of up to about sixteen hours. The potential health hazard of ethylene oxide further requires the use of specialized equipment usually available only in central specialized locations for ethylene oxide sterilization procedures.

Other sterilization methods successfully used in limited situations include chemical vapor sterilization, bacteriocidal chemical treatment, bead sterilizers and liquid disinfectant usage. Bleach, an available liquid disinfectant, while sterilizing many items effectively, also causes corrosion and color losses. No method heretofore readily available to occasional users will sterilize, without damage, items comprising materials such as corrodible metals, bleachable materials and heat deformable plastics.

The present invention concerns a readily available apparatus and method usable for dependable and rapid sterilization of a wide variety of items, including those comprising corrosion-prone metals, thermally deformable materials or instruments with critically close spatial tolerances.

Recent reports have shown that microwaves can be effective in the decontamination of foods [Billbrough, J. (1969) Food Sterilization by Microwave Radiation. Non-Ionizing Radiation V. 2 pp. 70–72; Culkin, K.A. and Fung D.I.C., (1975) Destruction of Escherichia coli and Salmonella typhimurium in microwave Cooked Soups. J. Milk Food Technol. V. 38, pp. 8–15]and in the bacterial decontamination of materials in a clinical microbiology laboratory [Latimer, J.M. and Matsen, J.M. (1977) Microwave Oven as a Method for Bacterial Decontamination in a Clinical Microbiology Laboratory, J. Clin. Microbiol. V. 6, pp. 340–342].

The ready availability and safety of microwave ovens has led the present inventors to seek and find a method and apparatus usable with microwave ovens for the sterilization of portable items therein.

Particular application of microwave oven sterilizations are too numerous to entirely include herein, but include the following situations. The owner of dentures may desire to sterilize said dentures to help alleviate conditions ranging from halitosis to candidiasis. A dentist or dentist's aide may desire to sterilize, between usages, dental handpieces—turbine driven drilling bur holders, or the burs themselves.

The above items exemplify items sterilizable in the apparatus and by the methods described as the present invention.

In many areas of science and medicine the fixation of eucaryotic cells upon a solid matrix is a necessary prelude to procedures such as cell staining, fluorescent labelling or radiographic labelling and subsequent microscopic or radioautographic examination. The examination of eucaryotic cells from tissue culture or from excised tumors are but two of many examples of situations where cell fixation is important.

As an alternative to usual fixation techniques such as heating or immersion in formalin solutions, several reports have indicated a demonstrative superiority for cell fixation by microwave irradiation (Zimmermal et al. Laboratory Medicine, December 1972, p. 29; Login, Amer. J. Med. Tech., V. 44, p. 435, 1978; Patterson et al., Stain Tech., V. 55, p. 71, 1980). When a uniform exposure of cell specimens to microwave irradiation is desired or required, the use of the apparatus and method comprising the presnt invention for such fixation is advisable. Microwave fixation upon glass plates of eucaryotic cells from a cell suspension has been found to result in greater retention on the glass plates of cells and of cell proteins than that seen with fixation by immersion in formalin solutions. This increased retention, it has been noted, is not always consistent, the likely cause of this inconsistency being uneven exposure of the cell-coated glass plates to microwave radiation.

The present invention concerns a method and apparatus useful for evenly exposing such cells to microwave irradiation for rapid, even and efficient fixation.

SUMMARY OF THE INVENTION

An apparatus for facilitating the exposure of items to microwave irradiation, the apparatus comprising a base; a plate having a substantially horizontal plane and being rotatably mounted on said base; a spit comprising an axis, a first spit end and a second spit end, the spit being turnably mounted on said plate and substantially axially parallel to the horizontal plane; a means for mounting said items upon said spit; a means for rotating said plate in the horizontal plane while turning said spit with said mounted items; and a means for determining a sterilization efficiency in said microwave oven. A method for sterilizing items or fixating cells emplaced within the above described apparatus.

BRIEF DESCRIPTION OF THE DRAWINGS

FIG. 1 is a top plan view of the apparatus of the present invention.

FIG. 2 is a side partial sectional view of the apparatus of the present invention.

FIG. 3 is an end partial sectional view of the apparatus of the present invention.

DETAILED DESCRIPTION OF THE PREFERRED EMBODIMENT

The present invention concerns an apparatus for facilitating the exposure of items to microwave irradiation. The heterogeneous distribution of microwave irradiation in commonly available microwave ovens presents a potential problem in using these ovens as sterilizers. These ovens will have areas of intense irradiation and areas of lower irradiation. The apparatus of the present invention is a device for rotating solid objects in a horizontal plane while turning these objects on a spit substantially axially disposed parallel to this horizontal plane. This mode of movement facilitates the exposure of items mounted on the spit to a plurality of irradiation areas within a microwave oven while turning these items end-over-end to substantially equalize the energies from the dominant microwave modes to all surfaces of the items to be sterilized or to have eucaryotic cells fixated thereon.

An apparatus for facilitating the exposure of items to microwave irradiation, for example in a microwave oven, is generally designated by the numeral 10 in FIGS. 1, 2 and 3. The apparatus 10 comprises a base 12, a plate 14 having a substantially horizontal plane 16 rotatably mounted on the base 12, and a spit 18. The spit 18 comprises an axis 20, a first spit end 22 and a second spit end 24. Also a part of the apparatus 10 is a container 26, composed at least primarily of a microwave-transparent material such as particular glasses, plastics or ceramics, for items to be sterilized, the container being mountable upon the spit 18. Any means adequate for retaining items to be sterilized or fixated upon the spit 18 such as elastic bands, clips or strings, suffice in the operation of the present invention, the container 26 being particularly preferable when a number of small items are to be sterilized. A means for rotating the plate 14 in a substantially horizontal plane 16 is seen in FIGS. 1 and 2 as comprising an electric motor 28 attached to the base 12. The electric motor 28 may be accompanied by batteries as an electrical source (not shown) or may be connected to an external source (not shown) of power. The electric motor 28 and any accompanying batteries are substantially enclosed in a microwave-reflective or absorbent covering 30. The electric motor 28 is gearingly adapted to turn a gear 32 mounted at a point 33 which in turn rotatingly drives the plate 14 in the horizontal plane 16.

The plate 14 is inset above a smooth portion 34 of the base 12. To facilitate the rotation of the plate 14, rollers 36 are rotatingly attached to the bottom 38 of the plate 14 to roll upon the smooth portion 34 of the base 12. The plate 14 has a mesh 40 on a plate peripheral outer edge 42. When the motor 28 is activated, the motor driven gear 32, meshingly engages the mesh 40 on the peripheral outer edge 42 of the plate 14 to rotate the plate 14 in the horizontal plane 16, the plate rollers 36, one of many possible types of rolling facilitators, allowing the plate 14 to freely rotate upon the smooth portion 34 of the base 12. To assure that the plate 14 is centrally maintained during rotation on the smooth portion 34 of the base 12 a peg (not shown) is affixed to the center of the bottom 38 of the plate 14 and rotatingly engages a hole (not shown) in the center of the smooth portion 34 of the base 12. Other obvious means of assuring such central maintenance of the plate 14 would include having a track (not shown) in the smooth portion 34 of the base 12 for guiding the rollers 36 during rotation of the plate 14.

As seen most clearly in FIG. 2 the spit 18 is turnably mounted on the plate 14 and is substantially axially parallel to the horizontal plane 16 of the plate 14. For mounting the spit 18, the plate 14 further comprises a first post 44 and a second post 46. These posts 44 and 46 are of about the same length and have upper post ends 48 and 48a and lower post ends 50 and 50a. The lower post ends 50 and 50a engage an upper plate surface 52 so that the posts 44 and 46 are substantially perpendicular to the horizontal plane 16 thereof. The posts 44 and 46, near the upper post ends 48 and 48a, turnably engage the spit 18. The first spit end 22 turnably engages the first post 44 near the upper post end 48. The spit 18, at a position 54 spaced from the second spit end 24, turnably engages the second post 46 near the upper post end 48a. The mode of mounting the spit is not crucial to the operation of this apparatus 10 since any means for attaching items to the spit 18 functions adequately.

The upper plate surface 52 comprises an adherent layering 53 of an absorber of S band waves, often referred to as radar absorbent material (RAM) and which also often characteristically absorbs microwaves. An absorber preferably usable as such a layering 53 is Eccosorb LS (Emerson and Cuming, Inc., 869 Washington St., Canton, Mass. 02021).

An absorber for microwave irradiation is advisably present when items are to be sterilized in a microwave oven. One type of absorber is a volume of water; however, this water must be monitored and supplemented to assure that total evaporation does not result in an unnoticed absence of absorber during a period of irradiation. If no absorber of microwave irradiation is present during usage of a microwave oven, a substantial proportion of the microwaves may return to the magnetron to be absorbed thereby and cause heating and breakdown thereof. Hence, during the sterilization of substantially non-microwave absorbent items, a microwave absorber should be included in the microwave oven chamber. A further advantage of having a microwave absorber, such as the layering 53 on the upper plate surface 52 of the apparatus 10 of the present invention, is that it lowers the microwave-induced buildup of potential electrical charge upon metal items such as dental handpieces or drilling burs so that electrical arcing is less likely to occur during microwave sterilization of such metal items.

The apparatus 10 also comprises a wheel 56 being disposed in a substantially vertical plane 58. The wheel 56 has a wheel center 60 with spokes 62, 62a and 62b connecting the wheel center 60 to a peripheral wheel edge 64. The wheel center 60 is attached to the spit 18 near the second spit end 24. The peripheral wheel edge 64 has a serrulate wheel edge surface 66.

The base 12 preferably has a raised periphery 68 with a serrulate peripheral surface 70. The wheel 56 is positioned so that the serrulate wheel edge surface 66 meshingly engages the serrulate peripheral surface 70 of the base 12, as seen most clearly in FIG. 3.

Thus, when the electric motor 28 is activated, the plate 14 is rotatingly driven by the gear 32 and the meshing engagement of the serrulate wheel edge surface 66 with the serrulate peripheral surface 70 of the base 12 causes the spit 18 and container 26 mounted thereon to turn while rotating with the plate 14.

Items to be sterilized or slides of cells to be fixed may be placed in the container 26 of the apparatus 10 or otherwise mounted on the spit 18 and situated in a common microwave oven. The electric motor 28 is activated, the oven is activated and the items are rotatingly transported while turning end-over-end. The items pass through spaces varying in microwave irradiation, thus substantially equalizing the energies from the dominant mode of microwave irradiation to all surfaces of the items as these items are exposed to these spaces with different surfaces of the items being alternately exposed by the spit 18 and container 26 turning action. The turning action is particularly important to sterilize items not transparent to microwave irradiation since the current buildup on the surface of these items will seek the shortest path of travel and accelerate at that point and not over the entire surface.

The apparatus 10 with the exception of the motor 28 is preferably constructed essentially of polymeric organic materials, particularly preferred are those polymeric organic materials substantially transparent to microwave irradiation.

The container 26 is preferably openable and removably mounted on the spit 18 to facilitate emplacement and removal of items.

A calibration kit, usable to determine a sterilization efficiency in a microwave oven, comprises a set of sealed vials, preferably composed of a plastic or glass, both of these exemplifying materials which should be microwave transparent and visually, at least translucent. These vials have an enclosed volume preferably of between about 0.5 cc and 5.0 cc and are internally sterile, except for an included paper strip containing viable spores of one or more species of non-pathogenic microorganisms. These viable spores should be germinable in a nutrient growth medium at ambient temperatures of offices, laboratories or homes. Examples of such usable spores are available from microorganisms such as *Bacillus pumilis* and *Bacillus subtilis,* in addition to many other microorganisms well known in fields of microbiology.

The vials containing the spore strips will preferably have plastic peelable seals covering a soft needle-penetrable stopper. The spore strip-containing vials preferably will be partially evacuated of air, for reasons later described.

Another component of the calibration kit is a set of sealed, sterile tubes containing a clear liquid bacterial culture medium having a pH between about 6.5 and 7.5. Each tube has a mounted hypodermic needle, covered with plastic wrapping. In one embodiment, the culture medium contains a pH sensitive dye such as about 0.005% acid fuchsin which is essentially colorless at a near neutral pH and becomes pink at an acidic pH.

In utilization of the kit, the spore-containing vials are subjected to conditions of sterilization, for example, to microwave irradiation in a container 26 mounted on a turning spit 18 and on a rotating plate 14 according to the method and apparatus of the present invention. In one particular use of the calibration kit, about five spore-containing vials would be placed in the operating microwave oven and a vial removed after exposure to irradiation for increments of, for example, 4, 6, 8, 10 and 12 minutes. One vial will be unexposed to any irradiation and used as a control.

Each vial will then be mated with an inverted tube of culture medium by removal of the needle plastic cover and insertion of the inverted tube needle into the partially evacuated vial.

The vials, now containing microwave irradiated spore strips immersed in culture medium will be incubated at ambient temperatures for at least one day and the germination of any viable spores permitted to ensue. The growth of microorganisms from the spores in the vials, particularly the unirradiated control will be accompanied by microorganism growth indicators such as a visually observable turbidity or a pink coloration as acid metabolites are produced. If no pH sensitive dye is included in the tubes of culture medium, the appearance of turbidity alone would frequently suffice as a visual growth indicator.

It is expected that different types of microwave ovens as well as different modes of vial exposure to microwave irradiation will result in different periods of microwave radiation for spore sterilization.

In practice after the withdrawal of the spore-containing vials from a microwave oven, culture medium addition to said vials, and the incubation for a period of, for example, one day, there should be vigorous growth in the control vial, and less to no growth in microwaved vials. For example, if the vial microwaved for 8 minutes shows no microorganism growth, then an 8 minute sterilization time for items such as dentures or dental handpieces would be indicated as minimal. To even more assuredly sterilize such items, their time of microwave exposure should be extended, in the above example, to perhaps sixteen minutes.

Currently under consideration for further development is a microwave sensitive inidcator tape which could be affixed, for example, to paper packages of items to be microwave-sterilized. The indicator tape would preferably change its appearance, in color or pattern, upon exposure to a dose of microwaves sufficient to sterilize items enclosed in said package. Such an indicator tape may comprise a material such as 3 M Type 458 Thermographic paper (CTN S786 14580013) which exhibits heat sensitive visually observable changes.

When a sample of the type 458 Thermographic paper was first lightly sprayed with particulate carbon and then subjected to microwave irradiation, the characteristic visually observable changes were found to occur. The period of irradiation necessary to cause these changes were qualitatively found to inversely relate to the amount of particulate carbon applied to the paper.

The use of such a microwave-sensitive visually changing tape, analogous to the use of commonly employed autoclave indicator tape in autoclaving, would allow users of microwave sterilization to visually perceive microwave-treated items or containers thereof.

An apparatus similar to the apparatus 10 described herein but having independent motors for turning the spit and rotating the plate thereof, was utilized in a series of sterilization studies as described in the following Examples. In all these Examples a microwave oven (Toshiba no. ER-899BT-1) was utilized at 720 watts power and a beaker of water was included in the oven as a microwave absorbent.

EXAMPLE 1

Sterilization of Contaminated Plastic Test Tubes

Aqueous suspensions containing at least 100,000 cells per ml were individually prepared with the following organisms: *Staphylococcus aureus; Staphylococcus epidermidis; Klebsiella pneumoniae; Candida albicans; Bacillus subtilis* (aerobic spore former); and *Clostridium histolyti-*

*cum* (anaerobic spore former). A small volume of each suspension was used to coat the interior surface of separate plastic test tubes. After excess suspensions were removed, the test tubes were air dried for about five minutes to produce coated test tubes. The anaerobic organisms were handled under oxygen free conditions. In one case, paper strips impregnated with *Bacillus subtilis* spores were placed in several test tubes.

The air-dried coated test tubes and the spore strip-containing test tubes were placed near the bottom surface of the microwave oven and subjected to microwave radiation for periods ranging from 0 minutes to ten minutes. After these periods of microwave irradiation, the test tubes were capped with sterile plugs after the addition of sterile nutrient broth (Brain-Heart Infusion Broth, Difco) and incubated at 37° C. Microorganism growth was evaluated after 24 hr. and 48 hr. incubations by qualitative observations of nutrient broth turbidity. While 8 minutes of radiation often resulted in test tube sterility, these results were only inconsistently reproducible. In a separate experiment, when coated and spore strip-containing tubes were placed in a container mounted on a turning and rotating spit and the microwave radiations, nutrient broth additions and incubations repeated; consistent and reproducible sterilizations were obtained in all cases after about 10 minutes of microwave radiation.

EXAMPLE II

Sterilization of Artificial Dentures

Individual acrylic dentures were submerged in the microorganism suspensions described in Example I for periods of 5 minutes, 1 day and 1 week, air dried, subjected to microwave radiation and submerged in the sterile nutrient broth as described in Example I. Again an inconsistent sterilization was obtained by static placement of the dentures in the microwave oven. When air dried microorganism-coated dentures were subjected to microwave radiation for 8 minutes while being turningly rotated, a consistent sterilization was obtained, even with the fungus *Candida albicans*. Acrylic dentures were submerged in a mixed suspension of *Staphylococcus aureus*, *Staphylococcus epidermidis*, *Klebsiella pneumoniae* and *Bacillus subtilis*, each at a concentration of 100,000 cells per ml, and air dried. A turningly rotating microwave radiation for 10 minutes of these air dried dentures resulted in complete and reproducible sterilization thereof.

EXAMPLE III

Sterilization of Dental Burs

Dental burs, small pointed metallic objects having both diamond and carbide drilling tips, were submerged in the mixed suspension described in Example II, air dried and placed in a clear plastic bag. A turningly rotating subjection to microwave radiation for 10 minutes resulted in a complete and reproducible sterilization, which was determined as described in Examples I and II.

EXAMPLE IV

Sterilization of Dental Air Turbine Handpieces

The mixed suspension of microorganisms described in Example II was applied to dental air turbine handpieces by two methods. One method was the submersion of the handpieces in the suspension and the second method was swabbing the handpieces with the suspension, either including or excluding the handpiece orifices. The suspension-treated handpieces were irradiated for 10 minutes, either statically or while being turningly rotated. Complete sterilization was reproducibly attained only on the handpieces that were contaminated by swabbing and only after the handpieces were microwaved during a turning rotation. When handpieces were submerged in the suspension, a non-reproducible sterilization was obtained, presumably because the suspension sometimes permeated these handpieces through orifices therein to reach microwave inaccessible spaces within the handpieces.

EXAMPLE V

Sterilization of Virus-Contaminated Dental Air Turbine Handpieces

Aqueous suspensions of polio type I virus and herpes simplex type 1 virus containing about 100,000 viruses per ml were prepared and mixed with an equal volume of human blood. Dental handpieces were swabbed with the blood-virus mixture and immediately exposed to microwave radiation while turningly rotating. The microwave-radiated handpieces were then eluted by washing with a small volume of sterile isotonic saline solution and the resultant eluent added to suspensions of viable Vero or Hep 2 human cells contained in a tissue culture vessel. The cytopathic effects of these eluents upon the human cells were microscopically observed after an incubation for 72 hrs. It was found that the eluent from handpieces which were radiated for 3 minutes had no cellular cytopathic effects and were thus sterilized of viruses. The eluent from unirradiated virus-contaminated handpieces caused cellular cytopathy.

EXAMPLE VI

Dimensional Stability of Radiated Acrykuc Dentures

The dimensional stability of acrylic dentures exposed to microwave radiation was evaluated using standard dental procedures for measuring said dimensional stability. Vertical stability was evaluated by analyzing the fit of the denture into impressions which had been made with the denture before its microwave radiation. The most accurate die stone available was used to make these impressions. Horizontal stability was evaluated with a measuring microscope capable of analyzing three points on the denture with a precision of about 1 micron.

Dentures in both a wet state and a dry state were exposed to microwave radiation and no dimensional changes were noted. A particular denture was exposed 100 times for 8 minute periods of microwave radiation and no dimensional change was detected with this denture.

EXAMPLE VII

Effect of Microwave Radiation upon the functionality of Dental Air Turbine Handpieces The ability of a dental air turbine handpiece to properly operate was determined after twenty-five 10 minute exposures to microwave radiation. After such radiations, it was found that the handpiece exhibited no noticeable loss of power and no functional aberrations.

Changes may be made in the construction, operation and arrangement of the various parts, elements, steps and procedures described herein without departing from the concept and scope of the invention as defined in the following claims.

What is claimed is:

1. an apparatus for facilitating the exposure of substantially all surfaces of items to microwave irradiation to sterilize said items when said apparatus is disposed in a space and subjected to microwave irradiation from a source of microwave irradiation wherein the microwave irradiation energies varies within said space, the apparatus comprising:

a base;

a plate rotatably mounted on said base;

a spit turnably mounted on said plate a distance generally above said plate;

means for mounting said items upon said spit; and means for rotating said plate in a plane while simultaneously turning the spit with said items mounted thereon to turn said items in a plane angularly disposed with respect to the plane in which the plate is rotated, so the items to be sterilized are rotated in one plane by the plate being rotated in one plane or rotation and simultaneously turned in another plane which is angularly disposed with respect to the planar disposition of said first-mentioned plane by the turning of said split to substantially equalize the energies from the source of microwave irradiation to all surfaces of the items to be sterilized when said apparatus containing said items is disposed in said space and subjected to microwave irradiation with said space to sterilize said items.

2. The apparatus of claim 1 wherein the means for rotating the plate is defined further as comprising: an electric motor attached to the base; and a source of electricity connected to said electric motor.

3. The apparatus of claim 2 wherein the motor and the source of electricity are defined further as being substantially shielded from microwave irradiation.

4. The apparatus of claim 1 wherein the means for mounting is defined further as comprising a container mounted on said spit.

5. The apparatus of claim 4 wherein the container is defined further as being openable and removably mounted upon the spit.

6. The apparatus of claim 1 wherein the base is defined further as having a raised periphery with a serrulate peripheral surface and the plate is defined further as substantially covering said base while leaving exposed said serrulate peripheral surface.

7. The apparatus of claim 6 wherein the plate is defined further as comprising an upper plate surface.

8. The apparatus of claim 7 wherein the plate is defined further as comprising a first post and a second post.

9. The apparatus of claim 8 wherein the posts are defined further as being of about the same length and as having lower post ends and upper post ends.

10. The apparatus of claim 9 wherein the lower post ends are defined further as engaging the upper plate surface so that the posts are substantially perpendicular to the horizontal plane thereof.

11. The apparatus of claim 10 wherein the spit is defined further as having a first spit end and a second spit end and the posts are defined further as turnably engaging the spit near the upper post ends.

12. The apparatus of claim 11 wherein the first spit end is defined further as turnably engaging the first post near the upper post end.

13. The apparatus of claim 12 wherein the spit is defined further as being turnably engaged, at a position spaced from the second spit end, to the second post near the upper post end.

14. The apparatus of claim 13 defined further to include a wheel being disposed in a substantially vertical plane and as having a wheel center and a peripheral wheel edge.

15. The apparatus of claim 14 wherein the peripheral wheel edge is defined further as having a serrulate wheel edge surface to meshingly engage the serrulate peripheral surface of the base and the spit is defined further as being attached near the second spit end to the wheel center so that when the plate is rotated the spit with the mounted container turns.

16. The apparatus of claim 1 wherein the base, plate and spit are defined further as consisting essentially of polymeric organic material.

17. The apparatus of claim 1 wherein the means for rotating said plate and simultaneously turning said spit is defined further as rotating said plate in the plane which is a substantially horizontal plane while simultaneously turning said spit for turning said items in a plane substantially parallel with the horizontal planar disposition of the rotating plate for turning the items in the plane which is about perpendicular to the horizontal first-mentioned plane.

18. A process for facilitating the exposure of substantially all surfaces of items to microwave irradiation to sterilize said items when said apparatus is disposed in a space and subjected to microwave irradiation from a source of microwave irradiation wherein the microwave irradiation energies vary within said space, utilizing an apparatus for containing the items to be sterilized wherein the apparatus is adapted to rotate the items in one plane and simultaneously turn the items in another plane angularly disposed with respect to the first-mentioned plane, the process comprising the steps of:

placing the items to be sterilized upon the apparatus;

placing the apparatus with the items to be sterilized placed thereon in said space; and rotating the items to be sterilized utilizing said apparatus in one plane of rotation and simultaneously turning the items to be sterilized in another plane which is angularly disposed with respect to the first-mentioned plane while subjecting the items to be sterilized to microwave irradiation for a predetermined period of time to produce irradiated items, so the items to be sterilized are simultaneously rotated in one plane and in another plane which is angularly disposed with respect to the planar disposition of said first-mentioned plane to substantially equalize the energies from the source of microwave irradiation to all surfaces of the items to be sterilized when the apparatus containing said items is disposed in said space and subjected to microwave irradiation within said space to sterilize said items.

19. The process of claim 18 wherein the predetermined period of time is defined further as being about the time found necessary to sterilize bacterial spores contained in a vial emplaced in the apparatus.

20. The process of claim 18 wherein the items are defined further as comprising eucaryotic cells and the irradiated items are defined further as comprising fixated eucaryotic cells.

21. The process of claim 18 wherein the apparatus if further defined as being adapted to rotate the items in the first-mentioned plane which is substantially a horizontal plane and simultaneously turn the items to be sterilized about the other plane which is substantially perpendicular to the horizontal planar disposition of the first-mentioned plane.

* * * * *

UNITED STATES PATENT AND TRADEMARK OFFICE
CERTIFICATE OF CORRECTION

PATENT NO. : 4,599,216

DATED : July 8, 1986

INVENTOR(S) : Michael D. Rohrer, et al.

It is certified that error appears in the above-identified patent and that said Letters Patent is hereby corrected as shown below:

Column 8, Line 37, in the heading the word "acrykuc" should be deleted and the word --acrylic-- should be substituted.

Column 9, Line 24, please delete the word "split" and therefor substitute the word --spit--.

Signed and Sealed this

Ninth Day of December, 1986

*Attest:*

DONALD J. QUIGG

*Attesting Officer*  *Commissioner of Patents and Trademarks*